(12) United States Patent
Martin et al.

(10) Patent No.: US 8,089,279 B2
(45) Date of Patent: Jan. 3, 2012

(54) METHOD FOR OPERATING A HYBRID MEDICAL IMAGING UNIT COMPRISING A FIRST IMAGING DEVICE OF HIGH SPATIAL RESOLUTION AND A SECOND NUCLEAR MEDICINE IMAGING DEVICE OF HIGH SENSITIVITY

(75) Inventors: Diana Martin, Herzogenaurach (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 281 days.

(21) Appl. No.: 12/003,138

(22) Filed: Dec. 20, 2007

(65) Prior Publication Data

US 2008/0174310 A1   Jul. 24, 2008

(30) Foreign Application Priority Data

Dec. 22, 2006   (DE) .......................... 10 2006 061 320

(51) Int. Cl.
*G01V 3/00*   (2006.01)

(52) U.S. Cl. ........................................ 324/309; 324/307

(58) Field of Classification Search .......... 324/300–322; 600/410–435
See application file for complete search history.

(56) References Cited

U.S. PATENT DOCUMENTS

| | | | |
|---|---|---|---|
| 4,939,464 A * | 7/1990 | Hammer ........................ | 324/318 |
| 6,529,762 B1 | 3/2003 | Ladebeck | |
| 6,927,406 B2 * | 8/2005 | Zyromski .................. | 250/496.1 |
| 6,946,841 B2 * | 9/2005 | Rubashov ..................... | 324/318 |
| 7,154,096 B2 | 12/2006 | Amano | |
| 7,187,169 B2 * | 3/2007 | Clarke et al. .................. | 324/307 |
| 7,218,112 B2 * | 5/2007 | Ladebeck et al. ............. | 324/318 |
| 7,286,867 B2 * | 10/2007 | Schlyer et al. ................ | 600/407 |
| 7,323,874 B2 * | 1/2008 | Krieg et al. .................... | 324/318 |
| 7,482,592 B2 * | 1/2009 | Krieg et al. ............. | 250/363.04 |
| 7,522,952 B2 * | 4/2009 | Krieg et al. ................... | 600/411 |
| 7,626,389 B2 * | 12/2009 | Fiedler et al. ................ | 324/309 |
| 7,787,671 B2 * | 8/2010 | De Leon et al. .............. | 382/128 |
| 7,876,938 B2 * | 1/2011 | Huang et al. .................. | 382/128 |
| 2005/0154292 A1 | 7/2005 | Tank | |

FOREIGN PATENT DOCUMENTS

| | | |
|---|---|---|
| CN | 1608588 A | 4/2005 |
| DE | 19943404 | 4/2001 |
| DE | 19943404 A1 | 4/2001 |
| DE | 10357203 | 7/2005 |
| DE | 10357203 A1 | 7/2005 |
| WO | WO 03003038 A1 * | 1/2003 |
| WO | WO 2006071922 A2 * | 7/2006 |

OTHER PUBLICATIONS

C.Vollmar, "Bildfusion von MRT and ECD-SPECTT-Daten des menschlichen Gehirns", Dissertation LMU München, 2005, S.1-8; Others. German Patent Office Adtion dated Apr. 28, 2008.
Chinese Office Action dated Dec. 21, 2010 for corresponding Chinese Patent Application No. 2007101601462.

\* cited by examiner

*Primary Examiner* — Dixomara Vargas
(74) *Attorney, Agent, or Firm* — Harness, Dickey & Pierce, P.L.C.

(57) ABSTRACT

A method is disclosed for operating a hybrid medical imaging unit including a first imaging device of relatively high spatial resolution and a second nuclear medicine imaging device of relatively high sensitivity that respectively acquire imaging measurement signals from a common examination volume. In an embodiment of the method, during the current measurement signal acquisition of the second imaging device, the continuously acquired measurement signals are used to determine a region in the examination volume in which a region referred measurement signal acquisition is subsequently performed by the first examination device with use of a region referred measurement protocol.

20 Claims, 2 Drawing Sheets

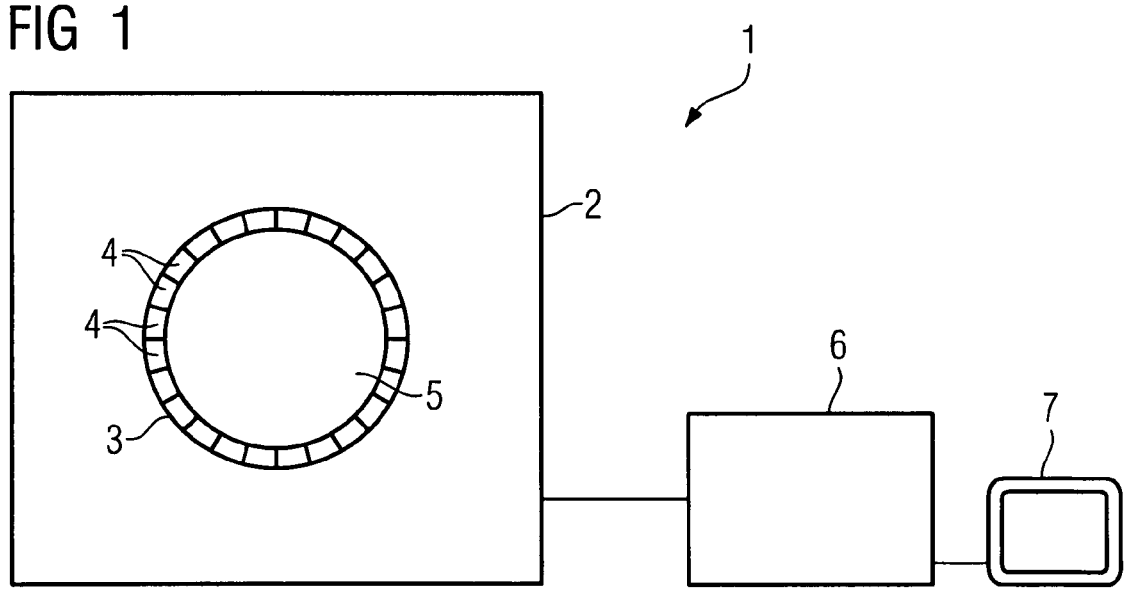

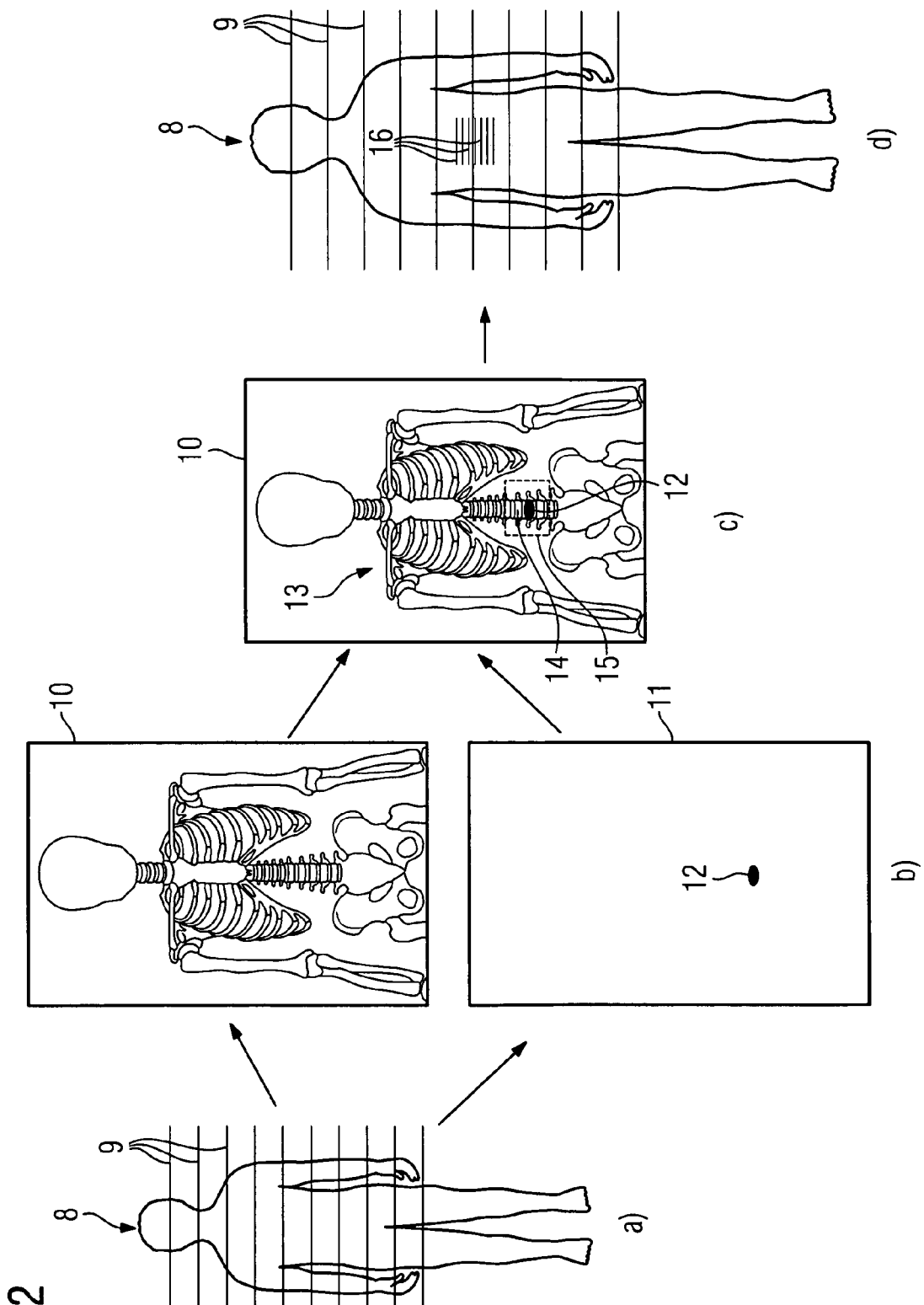

METHOD FOR OPERATING A HYBRID MEDICAL IMAGING UNIT COMPRISING A FIRST IMAGING DEVICE OF HIGH SPATIAL RESOLUTION AND A SECOND NUCLEAR MEDICINE IMAGING DEVICE OF HIGH SENSITIVITY

PRIORITY STATEMENT

The present application hereby claims priority under 35 U.S.C. §119 on German patent application number DE 10 2006 061 320.1 filed Dec. 22, 2006, the entire contents of which is hereby incorporated herein by reference.

FIELD

Embodiments of the invention generally relate to a method for operating a hybrid medical imaging unit. For example, the may relate to one including a first imaging device of relatively high spatial resolution and a second nuclear medicine imaging device of relatively high sensitivity that respectively acquire measurement signals from a common examination volume.

BACKGROUND

Hybrid imaging units are increasingly gaining importance in the field of medical imaging, this being so because they make it possible to be able to examine a patient in a very short time, sometimes even without repositioning, with the aid of two different modalities, that is to say to be able to compile image information with the aid of two different imaging devices. Such hybrid imaging units in this case include a first imaging device of relatively high spatial resolution, for example a computer tomograph or a magnetic resonance machine, and a second, in the present case, nuclear medicine imaging device of relatively high sensitivity for example for PET (position emission tomography) or SPECT (single photon emission computed tomography). Both methods are tomographic methods that show in the body the distribution of a radio nuclide, that is to say a radiopharmaceutical, given to the patient.

Such radio nuclides have the property of accumulating intensively at specific pathological zones. PET or SPECT imaging methods by mixing the acquisition of the radio nuclide distribution in the body, while corresponding images that finally show probability distributions and constitute an "activity card" can be determined from the acquired measurement signals and displayed. The mode of operation of these methods is known in principle, and there is no need to go into this in more detail.

It is particularly expedient to combine a first imaging device in the form of a magnetic resonance machine with a second imaging device in the form of a PET device. The point is that magnetic resonance tomography permits a very high spatial resolution, on the one hand, while not influencing PET measurement, on the other hand. As a result, it is possible to erase the PET detectors in the interior of the cylindrical patient aperture of a conventional magnetic resonance system such that both can measure using the same isocenter, and is even possible for both measurements to run simultaneously. The PET examination furthermore delivers very informative images, and this is to be ascribed to the production of the measurement signals (time-resolved detection of gamma quanta). What is involved here is a coincidence measurement method of high counting yield and thus of very high sensitivity.

Both the highly resolved image of the first imaging device, that is to say, for example, the MR image, and that of the second imaging device, that is to say, for example, the PET image, permits a subsequent evaluation with the aid of which it is possible to draw diagnostic conclusions that then require a follow-up examination in some cases, in order, for example, to examine again more precisely with the aid of the magnetic resonance machine a specific region displayed as relevant in the PET image. This is certainly directly possible in principle, but is time consuming. The imaging unit can consequently not be visualized optimally since it is occupied up to the end of the evaluation of the first image recording until it has been decided whether a follow-up examination is necessary or not.

SUMMARY

In at least one embodiment of the invention a method is specified for operating such a hybrid imaging unit that permits a more efficient imaging operation.

In at least one embodiment of the invention, a method is provided wherein, during the current measurement signal acquisition of the second imaging device, the continuously acquired measurement signals are used to determine a region in the examination volume in which a region referred measurement signal acquisition is subsequently performed by means of the first examination device with use of a region referred measurement protocol.

In the case of at least one embodiment of the inventive method, the image that can respectively be output is compiled or reconstructed continuously during the current measurement signal acquisition via the second imaging device, that is to say the PET scanner, for example, such that concrete information relating to the progress of the measurement signal acquisition is continuously present. This information is now decisive in influencing the following imaging operation of the first imaging device, that is to say, for example, the magnetic resonance system.

For example, if it emerges from the PET image that a pathological region has been detected on the basis of the increased radio nuclide accumulation, this region is then selected. Since this information is already present at a very early point in time, specifically still during the current operation of the second imaging device, thus PET scanner, for example, it is then possible to begin a follow-up examination of precisely this pathologic region of interest exceptionally soon. There is thus no longer a need for an expensive subsequent image evaluation with a time delay upon conclusion of the PET measurement; rather, it is possible to begin the follow-up examination at an extremely handy point in time, ideally already doing so even when the first imaging device is still in operation and is running its original first measurement protocol.

The follow-up examination or the second examination is then performed with the aid of the first imaging device with use of a region referred measurement protocol, that is to say a special measurement protocol is used that is expedient or optimized for examination of this region. It can thereby be ensured that the possibly pathological relevant region is acquired optimally by imaging technology such that the corresponding evaluation of the images, and thus the diagnosis, can also be performed soon.

Overall, at least one embodiment of the inventive method permits a substantially more efficient and time optimized operation of a hybrid medical imaging unit, and this is advantageous both for the user, as relevant information and images can already be present and be evaluated much earlier, and advantages also result for the patient, who is able to be examined optimally in terms of imaging technology in a much shorter time.

According to a first alternative of at least one embodiment of the invention, the continuously acquired measurement signals are analyzed several times or in a continuously automatic fashion, and the region is automatically determined, after which the region referred measurement signal acquisition is performed automatically. Here, thus, the currently already acquired measurement signals that is to say image relevant data, for example of the PET measurement, is either provisionally reconstructed in specific time intervals or generally a continuous fashion and automatically analyzed in order to determine a local accumulation of the radio nuclide. That is to say, the region is automatically determined in the PET image, both as regards its position and its geometry or size, in order then to be able to appropriately evaluate the corresponding region referred measurement protocol.

The determination of position is therefore possible straightaway as, for example, given the combination of a PET scanner with a magnetic resonance system the corresponding coordinate systems in which the images of the different imaging devices are recorded are referenced to one another such that, for example, it is possible to assign a point in the PET coordinate system directly to a corresponding correlated point in the MR coordinate system. After the magnetic resonance system has been employed as usual to record an overview image in order to determine the required attenuation correction of the later images, the corresponding anatomical assignment of the acquired PET region is possible straightaway.

In each case, the automatically acquired region is now used to begin and perform, also automatically, the processing of the second region referred measurement protocol on the part of the first imaging device, that is to say the MR system, for example. A quasi fully automatic operation thus results here. Of course, it is also conceivable to interpose a user interaction in such a way that before imaging is initiated the user is informed with use of the region referred measurement protocol and, for example, this further imaging is confirmed and cleared by giving an appropriate command via the control device.

In this case, according to a first alternative of at least one embodiment of the invention the automatic determination of region can be performed by ascertaining the signal intensity varying with the current signal acquisition, and comparing the signal intensity with a reference intensity value. Thus, the signal intensity, that is to say the brightness or the contrast of a region in the nuclear medicine image is automatically acquired, and a continuous comparison is made as to whether the intensity (brightness or contrast) overshoots a reference value, that is to say a threshold value, relative to the usual signal noise.

The image content thus determines the selection of region. The more that measurement signals can be acquired and be assigned to a specific region in the examination volume, the brighter and more intense does the region appear in the PET image. Since the nuclear medicine image is likewise resolved in pointwise fashion, there is, of course, the possibility here of specifically observing the signal intensity of image regions, for example by taking averages etc., in order not to analyze each individual pixel separately, although this would likewise be conceivable. It follows that how the intensity acquisition is configured as resolution criterion can differ from case to case.

In each case, the analysis of intensity or brightness permits a simple and accurate acquisition such that actually at least one point or very small region of very high signal intensity is given that is thus sufficiently bright or contrasted by comparison with the surroundings. The image processing device is then capable of determining from this information the actual region that is subsequently to be examined in more detail, something which is possible straightaway with the aid of the signal intensity profile, thus the brightness profile in the neighboring regions. That is to say, with the aid of the signal profiles and thus the image content it is possible to determine very accurately in the continuously reconstructed image the active region that belongs anatomically to the very small region in which a signal intensity exceeding threshold value was first acquired. Since this region can be acquired straightaway in position in its coordinate system because of the system correlation with the coordinate system of the magnetic resonance system, the corresponding region referred measurement protocol can be selected at once, and a start can be made on the region referred measurement.

As an alternative to determining region via the analysis of the signal intensities or the brightness distribution in the image, the automatic determination of region can be performed by comparing an image produced with the aid of the previously acquired measurement signals with a reference image of the examination volume. The reference image shows the examination volume more or less in the pathologically harmless state, in other words the normal activity of the examination volume. If, for example, it is found by image subtraction that the subtraction image shows a region that deviates substantially from the reference image, this can be recognized as a clear indication to the effect that what is involved is a region of increased activity substantiated by the increased radio nuclide accumulation. This region can also then be acquired exactly in anatomical terms, it thus being possible to recognize whether what is involved is a specific bone or a specific organ, whereupon the size and geometry realize the position of the region in the coordinate system can be automatically detected, in turn.

A determination of the region by the user is also conceivable as an alternative to automatically acquiring the region. To this end, it is possible, for example, to use the continuously acquired measurement signals to display a signal-dependent regional display exactly in position on a monitor in an overview image of the examination volume compiled by way of the first imaging device, the region being selected in the overview image by the user, after which the region referred measurement signal acquisition is performed. As described, this overview image of the first imaging device, that is to say the MR system, for example, is taken in any case in order to ascertain attenuation correction which may be required.

The image of the second imaging device, for example the PET image, is continuously reconstructed as described and can be displayed straightaway in the overview image accurately in terms of position and orientation after the imaging coordinate systems are referenced. The user therefore obtains a display of the overall image with the PET image painted in. He can immediately detect therefrom the continuous development of the PET measurement, and therefore immediately acquire a possibly pathologically relevant region which he then selects in the overview image or combination image, in which case he can thereby collect or vary the size or geometry of the region. He may make use to this end of, for example, appropriate input means such as a screen cursor or the like, in conjunction with possible graphic aids such as lines or boxes that he can thereby lay around the region in order to define the latter. The position and geometry of the region are then the decisive criteria for the subsequent selection of the region referred measurement protocol.

As already described, there is the particularly expedient possibility that the region referred measurement signal acquisition has already begun while the first imaging device is acquiring volume referred measurement signals in the examination volume with the use of another measurement protocol. A magnetic resonance system is capable straightaway of processing two different measurement protocols in parallel. This is to say, while measurement with the aid of the first measurement protocol is still running it is possible to process a second measurement protocol in order to record the region. While the first measurement protocol scans the entire examination volume with a specific number of slices, slice orientation, etc. it is already possible to begin the region referred measurement with an appropriate number of slices, selected specific to region, slice orientation, a measuring field specific to region, etc. Of course, it is also conceivable to undertake this region referred measurement directly following the ending of the first measurement operation of the first imaging device.

The region referred measurement protocol can be performed automatically with the aid of one or more selection criteria, in particular ones that can be or have been prescribed by the user, in particular an anatomical selection criterion. Thus, it is directly conceivable that the protocol selection is based on a medical problem. If, for example, the medical problem is to find bone metastases and a specific clinical picture of the patient, the region referred measurement protocol can be, for example, a special sequence for bone examination, that is to say use is made of a protocol optimized specifically with regard to the organ or body part to be examined. This protocol selection can be performed automatically, for example by automatically detecting after the examination of the region whether what is involved is a bone or the liver or another organ so that it is then possible to take account immediately of the appropriately optimized protocol. The corresponding selection criterion can be input by the user, for example as putative finding.

Finally, the planning and/or positioning of the region referred measurement protocol can be performed by the user or automatically. It is not only the selection of the measurement protocol fundamentally to be used as a basis to the effect of whether what is involved is a protocol for bone examination or for soft tissue examination etc. that can be defined either by the user or automatically, so too can concrete details such as for example, the number of slices or slice orientation or the size of the measurement field. This automatic protocol planning can be applied straightaway, particularly when use is made of a first imaging device with a so-called "auto-align function" in which the appropriate protocol settings are undertaken automatically. Such an auto-align function is described, for example, in DE 103 57 203 A1, the entire contents of which are hereby incorporated herein by reference. As an alternative thereto, it is, of course, also possible for the user to undertake the planning/positioning of the measurement protocol manually, for example in or with the aid of the overview image, the user being able in this case to directly set the number of slices and slice orientation etc.

In addition to the method itself, at least one embodiment of the invention further relates to a hybrid medical imaging unit comprising a first imaging device of relatively high spatial resolution and a second nuclear medicine imaging device of relatively high sensitivity which respectively acquire imaging measurement signals from a common examination volume, each imaging device preferably having a dedicated control device. The imaging unit is designed to carry out the method of the type described. To this end, the two separate control devices communicate with one another, for example, so that, by way of example, it is possible in the case of automatic acquisition of the region to give the appropriate information for one control device to the other which then, in turn, undertakes the protocol and planning selection etc. What is involved here in the case of the first imaging device is preferably a magnetic resonance device, while a PET device or a SPECT device is involved in the case of the second imaging device.

BRIEF DESCRIPTION OF THE DRAWINGS

Further advantages, features and details of the invention follow from the example embodiment described below as well as with the aid of the drawing, in which:

FIG. 1 shows an illustration of the principle of an inventive embodiment of a hybrid medical imaging unit, and FIG. 2 shows an illustration of the principle explaining the cause of an embodiment of the inventive method.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows an illustration of the principle of an inventive hybrid medical imaging unit 1 of an embodiment of the invention, including a first imaging device 2 of relatively high spatial resolution, a magnetic resonance device in the example shown. This is not illustrated in more detail, the basic design of such a magnetic resonance device being adequately known to a person skilled in the art and therefore not requiring anymore detailed explanation.

Provided, furthermore, is a second nuclear medicine imaging device 3, here in the form of a PET scanner including a number of individual detector elements 4 that are assembled to form a cylinder and clad the patient aperture 5. Their design and mode of functioning are likewise adequately known. The operation of the first and second imaging devices 2, 3 is controlled in the example shown via a central, common control device 6. It is possible with the aid of such an imaging device 1 to be able to simultaneously record MR images and PET images, since the magnetic resonance imaging does not influence the PET imaging, and vice versa. As described, the control device 6 controls the operation of the two imaging devices 2, 3 and undertakes to evaluate and process the recorded measurement signals, while any possible images are displayed by being output on a monitor 7.

The fundamental inventive mode of operation is illustrated in terms of principle in FIG. 2. What is shown is a patient 8 who has been brought in a fashion lying horizontally into the patient aperture 5 of the imaging unit 1. He is now simultaneously examined with the aid of the first imaging device 2 and the second imaging device 3 and corresponding measurement signals are simultaneously recorded. Illustrated in the left-hand figure marked with a) are the individual slice planes 9 in which the first imaging device, that is to say, the magnetic resonance device, records individual tomograms of the patient 8. It is to be seen that the slices are spaced relatively wide apart as is frequently customary for carrying out whole body imaging.

At the same time, the PET detector elements 4 acquire the measurement signals that result from the administration and the continuously increasing enrichment of radio nuclides, this not being shown in more detail in the illustration in accordance with a). In this case, gamma rays are detected via the detector elements 4, the respectively simultaneous beam inputs being evaluated at mutually opposite points of the PET imaging device 3. An increasing detection of events results in evermore individual measurement signals that can be evaluated, for example by ascertaining the probability distribution of the events on which the simultaneous detections are based such that it is possible overall to produce an activity card.

In the partial illustration marked by b), the upper region illustrates an overview image 10 such as is recorded via the magnetic resonance device 2. This overview image 10 is to be recorded of necessity, in order on the basis thereof to be able to ascertain and undertake an attenuation correction of images recorded thereafter.

Further illustrated is a PET image 11 such as can be produced via the PET device 3 with the aid of the continuous reconstruction and evaluation of the continuously recorded measurement signals. All measurement signals recorded up to now feature in this PET image 11, which can be developed further continuously with increasing measurement signal acquisition. Thus, it is possible for the development of the nuclide enrichment in the body to be continuously acquired and visualized. In the exemplary embodiment shown, it may be assumed that a region 12 of increased accumulation, that is to say a region of increased activity, has been ascertained.

The coordinate systems of the magnetic resonance device 2 and the PET device 3 are correlated with one another, that is to say each point in the examination volume scanned via the PET device 3 can be assigned exactly to a point in the examination volume scanned via the magnetic resonance device 2. It is thereby possible for the region 12, which is, for example, acquired in three dimensions, to be examined exactly in the overview image 10, which is likewise then acquired in three dimensions. As is illustrated in step c) the region 12 from the PET image 11 in the overview image 10 is now displayed accurately in terms of position and orientation in the overview image 10. The skeletal structure 13 of the patent 8, as well as the region 12 that lies in the region of and on the spinal cord 14 are to be recognized in the example shown.

This imaging can, for example, be displayed on the monitor 7 to the user, who can thereupon now localize the region 12 uniquely and recognize it as pathological. If this has not already been performed automatically, he can now, as shown by dashes in the display c), define a region 15, for example via the screen cursor in conjunction with a control mouse, etc., and define this region as for a directly following examination with the aid of a region referred measurement protocol on the part of the magnetic resonance device 2. As an alternative to the selection of the region undertaken by the user, this can also be performed entirely automatically. The common control device 6 would be capable of exactly determining the position of the region 12 in the examination volume of the magnetic resonance device 2, and thereupon the required measurement protocol would be capable of selecting or defining region referred remeasurement, for example with regard to the number of slices and slice orientation etc., in order to be able to record this possibly pathologically relevant region optimally in a second highly resolved, very accurate MR scan.

This automatic selection can also be performed, for example, with the aid of an anatomical selection criterion prescribed by the user. For example, it may be assumed that the user is assuming bone metastases, for which reason he is necessarily already defining as region referred measurement protocol to be selected inherently a region that includes specific bone examination sequences etc. The control device 6 now selects such a bone examination protocol and optimizes the latter, for example with regard to the particular number of slices, slice spacing and slice orientation as well as the measurement field that is required in order to dimension or cover the requisite region 15 about the pathological region 12 optimally. In the case of a manual determination of region by the user, the number of slices, slice spacing and orientation etc. can likewise be performed by the user, for example in the display in accordance with c), that is to say in the overview image 10.

The patient 8 is then examined—see the partial illustration d)—by means of the magnetic resonance device 2, specifically both with the aid of the first measurement protocol already running, as illustrated by the slices 9, and with the aid of the second region referred measurement protocol, as is illustrated by the substantially more closely lying slices 16, which actually lie in the region 15 firstly defined and resolve the latter optimally. The measurement signals continue likewise to be simultaneously acquired via the PET device 3 in order to further improve the PET image 11 as a consequence of the continuously rising number of measurement signals. In each case, however, it is possible to begin with the second MR measurement solely of the relevant region 15 at a very early point in time, so that upon conclusion of all the measurements a normal whole body image acquired with the aid of the magnetic resonance system 2 is available, while on the other hand so are the highly resolved, exceptionally informative image of the pathological region 15, as well as the nuclear medicine image, specifically the PET image 11.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating a hybrid medical imaging unit comprising:
   acquiring a first measurement signal through a first nuclear medicine imaging device of high sensitivity from a common examination volume; and
   using, during the acquiring, the continuously acquired current first measurement signal to determine a region within the common examination volume, wherein
   a second measurement signal specific to the region is subsequently acquired via a second magnetic resonance examination device of high spatial resolution, using a region referred measurement protocol and the first measurement signal from the first nuclear medicine imaging device.

2. The method as claimed in claim 1, wherein the continuously acquired measurement signals are analyzed at least one of several times and in a continuously automatic fashion, and wherein the region is automatically determined, after which the region referred measurement signal acquisition is performed automatically.

3. The method as claimed in claim 2, wherein the automatic determination of region is performed by ascertaining the signal intensity varying with the current signal acquisition, and comparing the signal intensity with a reference intensity value.

4. The method as claimed in claim 2, wherein the automatic determination of region is performed by comparing an image produced with the aid of the previously acquired measurement signals with a reference image of the examination volume.

5. The method as claimed in claim 1, wherein the continuously acquired measurement signals are used to display a signal-dependent regional display exactly in position on a monitor in an overview image of the examination volume compiled by the first imaging device, the region being selected in the overview image by the user, after which the region referred measurement signal acquisition is performed.

6. The method as claimed in claim 5, wherein at least one of the size and geometry of the region is at least one of selectable and variable by the user.

7. The method as claimed in claim 1, wherein the region referred measurement signal acquisition has already begun while the first imaging device is acquiring volume referred measurement signals in the examination volume with the use of another measurement protocol.

8. The method as claimed in claim 1, wherein the region referred measurement protocol is performed automatically with the aid of one or more selection criteria.

9. The method as claimed in claim 8, wherein the region referred measurement protocol is performed automatically with the aid of one or more selection criteria that can be or have been prescribed by the user.

10. The method as claimed in claim 9, wherein the one or more selection criteria include an anatomical selection criterion.

11. The method as claimed in claim 8, wherein the one or more selection criteria include an anatomical selection criterion.

12. The method as claimed in claim 1, wherein at least one of planning and positioning of the region referred measurement protocol is performed at least one of by the user and automatically.

13. A computer readable medium including program segments for, when executed on a computer device, causing the computer device to implement the method of claim 1.

14. A hybrid medical imaging unit, comprising:
   a first magnetic resonance imaging device of high spatial resolution; and
   a second nuclear medicine imaging device of high sensitivity, each of the first magnetic resonance imaging device and second nuclear medicine imaging device respectively being configured to acquire imaging measurement signals from a common examination volume, the first magnetic resonance imaging device being configured to use, during a first measurement signal acquisition of the second nuclear medicine imaging device from the common examination volume, the continuously acquired first measurement signal of the second nuclear medicine imaging device to determine a region within the common examination volume in which a second measurement signal specific to the region is subsequently acquired via the first magnetic resonance imaging device, using a region referred measurement protocol and the first measurement signal from the second nuclear medicine imaging device.

15. The hybrid medical imaging unit as claimed in claim 14, wherein the first imaging device is a magnetic resonance device, and the second nuclear medicine imaging device is a PET device or a SPECT device.

16. A hybrid medical imaging unit, comprising:
a first nuclear medicine imaging device;
a second magnetic resonance examination device;
means for acquiring a first measurement signal through the first nuclear medicine imaging device from a common examination volume; and
means for using, during the acquiring, the continuously acquired current first measurement signal, to determine a region within the common examination volume, the means for using and the nuclear medicine imaging device both being useable to acquire imaging measurement signals from the common examination volume, a second measurement signal specific to the region is subsequently acquired via second magnetic resonance examination device, using a region referred measurement protocol and the first measurement signal from the first nuclear medicine imaging device.

17. The hybrid medical imaging unit as claimed in claim 16, wherein the means for using includes a magnetic resonance device, and the second nuclear medicine imaging device is a PET device or a SPECT device.

18. A method for operating a hybrid imaging unit, comprising
acquiring a first measurement signal through a first nuclear medicine imaging device of high sensitivity from a common examination volume; and
determining a specific region in an examination volume common to the first nuclear medicine imaging device and a second magnetic resonance examination device of high spatial resolution, from the continuously acquired current first measurement signal, where the second magnetic resonance examination device acquires a second measurement signal related to the specific region using a region referred measurement protocol and the first measurement signal from the first nuclear medicine imaging device.

19. The method as claimed in claim 18, wherein the continuously acquired measurement signals are analyzed at least one of several times and in a continuously automatic fashion, and wherein the region is automatically determined, after which the region referred measurement signal acquisition is performed automatically.

20. The method as claimed in claim 19, wherein the automatic determination of region is performed by ascertaining the signal intensity varying with the current signal acquisition, and comparing the signal intensity with a reference intensity value.

* * * * *